US00PP20520P2

(12) United States Plant Patent
Steenland

(10) Patent No.: US PP20,520 P2
(45) Date of Patent: Dec. 1, 2009

(54) ***COPROSMA* PLANT NAMED 'LEMON AND LIME'**

(50) Latin Name: *Coprosma*
Varietal Denomination: Lemon and Lime

(75) Inventor: Ron Steenland, Boskoop (NL)

(73) Assignee: Growing Spectrum Ltd., Kihi Kihi, Walkato (NZ)

( * ) Notice: Subject to any disclaimer, the term of this patent is extended or adjusted under 35 U.S.C. 154(b) by 0 days.

(21) Appl. No.: 12/229,714

(22) Filed: Aug. 26, 2008

(51) Int. Cl.
*A01H 5/00* (2006.01)

(52) U.S. Cl. ..... Plt./226

(58) Field of Classification Search ..... Plt./263.1, Plt./226
See application file for complete search history.

(56) References Cited

OTHER PUBLICATIONS

UPOV-ROM GTITM, Plant Variety Database, 2009/01, GTI Jouve Retrieval Software, citation for 'Lemon and Lime'.*

* cited by examiner

*Primary Examiner*—Susan B McCormick Ewoldt
(74) *Attorney, Agent, or Firm*—Mark P. Bourgeois

(57) ABSTRACT

A new cultivar of *Coprosma* plant named 'Lemon and Lime' that is characterized by leaves that are yellow with green margins during the Summer and orange with green margins during the Winter.

1 Drawing Sheet

Botanical classification: *Coprosma*.
Variety denomination: 'Lemon and Lime'.

BACKGROUND OF THE INVENTION

The present invention relates to a new and distinct cultivar of *Coprosma* plant botanically known as *Coprosma* and hereinafter referred to by the cultivar name 'Lemon and Lime'.

The new cultivar was discovered in a cultivated area of Boskoop, The Netherlands in 2007. 'Lemon and Lime' was discovered as a naturally occurring branch mutation of *Coprosma* 'Evening Glow' (not patented).

Asexual reproduction by tip cuttings of the new cultivar 'Lemon and Lime' was first performed in 2007 in Boskoop, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Lemon and Lime'.

1. *Coprosma* 'Lemon and Lime' exhibits leaves that are yellow with green margins during the Summer and orange with green margins during the Winter.

The closest comparison cultivar is the parent plant *Coprosma* 'Evening Glow'. The new cultivar 'Lemon and Lime' is distinguishable from 'Evening Glow' by the following characteristics:

1. 'Lemon and Lime' has leaves that are orange with green margins in the winter. The leaves of 'Evening Glow' are green with tinges of orange, red and yellow in the winter.
2. 'Lemon and Lime' has leaves that are yellow with green margins in the summer. The leaves of 'Evening Glow' are red with dark green to purple margins in the summer.

BRIEF DESCRIPTION OF THE DRAWING

The accompanying photograph illustrates the distinguishing traits of *Coprosma* 'Lemon and Lime'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Lemon and Lime'. Data was collected in Waikato, New Zealand from 12 month old outdoor grown plants in 2.5 liter containers. The time of year was summer in the Southern Hemisphere and the average temperature range was 12 to 22 degrees Centigrade during the day and 4 to 16 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Lemon and Lime' has not been tested under all possible conditions and phenotypic differences may be observed with variations in environmental, climatic, and cultural conditions, however, without any variance in genotype.

Botanical classification: *Coprosma* 'Lemon and Lime'.
Use: Ornamental perennial, evergreen shrub.
Parentage: 'Lemon and Lime' is a naturally occurring branch mutation of *Coprosma* 'Evening Glow'.
Vigor: Moderate.
Growth rate: Slow.
Plant shape: Broad upright inverted triangle.
Growth habit: Freely branching, dense, bushy habit.
Hardiness: Tolerant to −3 degrees Centigrade.
Suitable container size.—2 to 4.5 liter container.

Height: Average 1 m in height.
Width: Average 1 m in width.
Propagation: Tip cuttings.
Root system: Fine and fibrous.
Lateral branches:
*Quantity.*—Approximately 20.
*Length.*—Average 15 cm.
*Diameter.*—Average 3 mm.
*Internode length.*—10 mm.
*Color* (*mature*).—Orange 165C.
*Strength.*—Strong.
*Pinching.*—Yes.
Foliage:
*Texture.*—Smooth, glossy.
*Leaf arrangement.*—Opposite.
*Leaf attachment.*—Sessile.
*Compound or single.*—Single.
*Leaf shape.*—Obovate.
*Leaf apex.*—Rounded.
*Leaf base.*—Rounded.
*Leaf length.*—Average 30 mm in length.
*Leaf width.*—12 mm in width.
*Pubescence.*—Absent.
*Leaf margin.*—Entire.
*Summer leaf color* (*upper surface*).—3B with an inner margin 140B and an outer margin 141C.
*Summer leaf color* (*lower surface*).—3B with an inner margin 140B and an outer margin 141C.
*Winter leaf color* (*upper surface*).—33B with an inner margin 144B and an outer margin 141A.
*Winter leaf color* (*lower surface*).—33B with an inner margin 144B and an outer margin 141A.
*Vein pattern.*—Pinnate.
*Vein color.*—165B.
*Durability of foliage to stress.*—Moderate to high.
*Stipules.*—Absent.
Flowers: Flowers have not been observed to date.
Disease and insect resistance: Plants of the new *Coprosma* have not been observed for disease or insect resistance.

The invention claimed is:

1. A new and distinct variety of *Coprosma* plant named 'Lemon and Lime' as described and illustrated.

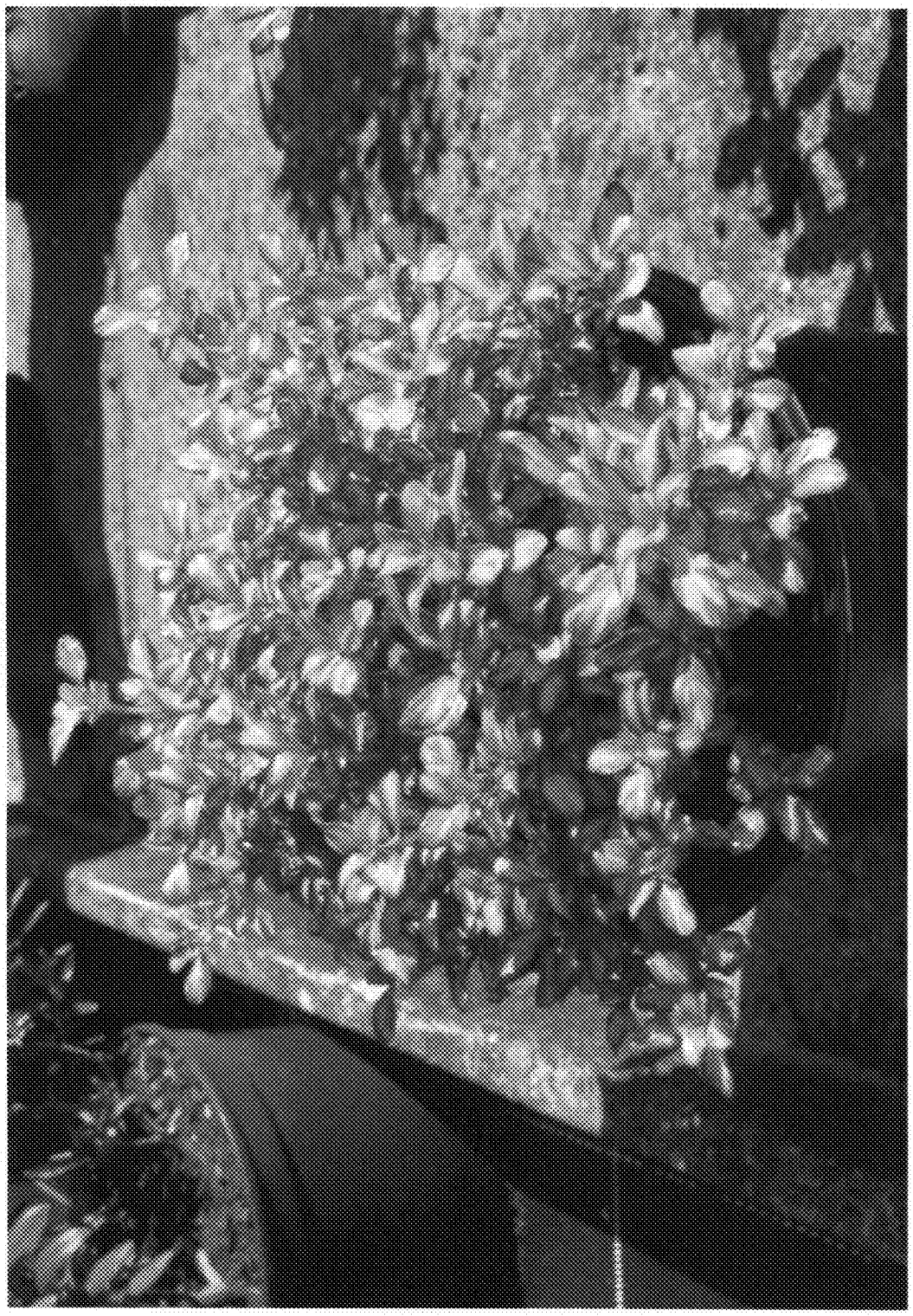

* * * * *